(12) United States Patent  
Frank et al.

(10) Patent No.: US 6,436,122 B1
(45) Date of Patent: Aug. 20, 2002

(54) HANDLE FOR A MEDICAL INSTRUMENT

(75) Inventors: Timothy Graham Frank, Dundee (GB); Uwe Bacher, Tuttlingen (DE); Alfred Cuschieri, Dundee (GB)

(73) Assignee: Karl Storz GmbH & Co. KG (DE)

( * ) Notice: Subject to any disclaimer, the term of this patent is extended or adjusted under 35 U.S.C. 154(b) by 180 days.

(21) Appl. No.: 09/653,776

(22) Filed: Sep. 1, 2000

Related U.S. Application Data

(63) Continuation of application No. PCT/EP00/01788, filed on Mar. 2, 2000.

(30) Foreign Application Priority Data

Mar. 17, 1999 (DE) .......................................... 199 12 038

(51) Int. Cl.⁷ ............................................... A61B 17/28
(52) U.S. Cl. ..................................................... 606/208
(58) Field of Search ................................ 606/205, 206, 606/208, 210, 170, 174, 151, 51, 52

(56) References Cited

U.S. PATENT DOCUMENTS

| | | | |
|---|---|---|---|
| 5,250,073 A | 10/1993 | Cottone, Jr. ................ | 606/206 |
| 5,792,178 A | * 8/1998 | Welch et al. ............... | 606/208 |
| 5,954,746 A | * 9/1999 | Holthaus et al. ............ | 606/208 |
| 5,976,121 A | 11/1999 | Matern et al. ................ | 606/1 |
| 6,077,286 A | 6/2000 | Cuschieri et al. ........... | 606/170 |

FOREIGN PATENT DOCUMENTS

| | | |
|---|---|---|
| DE | 43 18 019 A1 | 12/1994 |
| DE | 44 31 561 A1 | 3/1996 |
| DE | 196 18 291 A1 | 1/1998 |
| DE | 196 32 135 A1 | 2/1998 |
| DE | 297 01 910 U1 | 7/1998 |
| JP | 10151137 A | 6/1998 |

* cited by examiner

Primary Examiner—Kevin T. Truong
(74) Attorney, Agent, or Firm—St. Onge Steward Johnston & Reens LLC

(57) ABSTRACT

A handle is provided for a medical instrument comprising at least one movable grip element and a coupling portion through which a shaft is or can be connected with the handle. The movable grip element is or can be joined with a force transmission element axially movable in the direction of the longitudinal axis of the shaft to translate motion of the at least one movable grip element into linear motion of the force transmission element. The coupling portion is pivotal relative to a handle axis about at least one pivot axis running transversely to the longitudinal axis of the shaft. In addition, the movable grip element is or can be joined with the force transmission element through a lever arrangement comprising at least two double-arm levers. The first lever is pivotal about an axis fixed to the handle and the second lever is pivotal about an axis fixed to the coupling portion. The two levers are frictionally joined with one another and are pivotal with respect to one another about the first pivot axis.

18 Claims, 6 Drawing Sheets

HANDLE FOR A MEDICAL INSTRUMENT

CROSS REFERENCE TO PENDING APPLICATION

This is a continuation of pending International Application PCT/EP00/01788 filed on Mar. 2, 2000, which designates the United States.

BACKGROUND OF THE INVENTION

The invention generally relates to a handle for a medical instrument comprising at least one movable grip element and a coupling portion through which a shaft can be or is joined with the handle. The movable grip element is joined or can be joined with a force transmission element axially movable in the direction of the longitudinal axis of the shaft for translating motion of the at least one movable grip element into a linear motion of the force transmission element.

Such a handle is known for example from the German firm catalogue of the company Karl Storz GmbH & Co., Tuttlingen, "Karl Storz-Endoskope", volume "Endoskopische Chirurgie", second edition January 1994, page DGC 5/1 A.

Medical instruments are employed for various types of surgical operations on the human and animal body, in particular in minimal invasive surgery. Such instruments, for example tubular shaft instruments, can be configured as forceps, for example preparing or grasping forceps, forceps for cutting tissue, or as stamping or punching tool or the like. Depending on their varying function, the instruments differ in the corresponding configuration of the tools at the distal end. Cutting, grasping or punching tools can be provided at the distal end, where such an instrument comprises at least one movable tool, for example in the form of a jaw or a jaw part. However, such instruments can also comprise two or more movable tools at the distal end.

The instruments have a handle at the proximal end of the shaft to actuate the at least one movable tool. The shaft of the instrument is normally releasably or non-releasably joined with a coupling portion of the handle. In addition, the handle comprises at least one movable grip element for providing the actuation of the at least one movable tool at the distal end of the shaft. To actuate the at least one movable tool at the distal shaft end, the at least one movable grip element of the handle is joined in force-locking manner with the at least one movable tool through a force transmission element axially movable in the direction of the longitudinal axis of the shaft, for example a push and pull rod. Thus, motion of the movable grip element, for example a rotation or axial motion, is translated into axial relative motion of the force transmission element with respect to the shaft and finally motion of the movable tool.

A handle of the above-mentioned type is known in various configurations. The handle usually comprises a second grip element which is either stationary and fixed to the shaft or is also movable. Such a handle can also be formed as a scissors handle, where the two grip elements extend sidewards from the shaft of the instrument, as illustrated in the above-mentioned company brochure. In the sense of the present invention, the handle however can also be formed like a pistol grip element or like a bar grip element held in the fist of one hand.

Common to all these types of handles is that the handles in the joined condition with the shaft have a fixed, invariable angular position with respect to the shaft, i.e. the handle axis and the longitudinal axis of the shaft form a fixed angle with respect to one another.

However, a handle having a fixed angle with respect to the axis of the shaft is not always adapted to the requirements of the operating doctor with respect to its handling properties. Different doctors prefer different grip element orientations of the same type of handle with respect to the shaft depending on what they are accustomed to. To always have the handle with the optimal ergonomic angular position with respect to the shaft, it would therefore be necessary to have a set of several handles for each type of handle, which have different angular positions when joined with the shaft, so that the doctor can select the most ergonomic and optimal handle for himself. If the handles are not exchangeable, this means that for each instrument, an entire set of such instruments with differently angled handles must be available.

In addition, it can be desirable or necessary in some cases that the handle of the same instrument should take on different angular positions with respect to the shaft during the operation to have the most comfortable and therefore safest hand position for the operation procedure to be carried out. This would mean with the known handles, assuming a complete set were available, that the handle would have to be exchanged several times during the operation or with the nonexchangeable handles, the entire instrument would have to be exchanged which would substantially prolong the operation.

Accordingly, the known handles have disadvantages with respect to their ergonomic properties.

The object of the present invention is therefore to provide an improved handle of the above-mentioned type, which allows an ergonomic handling of the instrument, without having to exchange the handle or possibly even the entire instrument.

SUMMARY OF THE INVENTION

This object is achieved according to the invention by providing a handle for a medical instrument, comprising:

at least one movable grip element for being joined with a force transmission element axially movable in direction of a longitudinal axis of a shaft of said instrument to transfer motion of said at least one movable grip element into linear motion of said force transmission element;

a coupling portion for joining said shaft with said handle, said coupling portion being pivotal relative to a handle axis about at least one first pivot axis running transversely to the longitudinal axis of said shaft;

a lever arrangement for joining said at least one movable grip element with said force transmission element, comprising at least two double-arm levers, a first lever of which being pivotal about a first axis stationary with respect to said handle and a second lever of which being pivotal about a second axis stationary with respect to said coupling portion, and said two levers being joined to another to be pivotal with respect to one another about said first pivot axis.

According to the invention, the coupling portion through which the handle is joined or can be joined with the shaft is pivotal, so that the handle can be disposed in different angular positions with respect to the shaft. Preferably, the adjusted angle of the handle can be locked for rigid connection of the shaft to the handle to then employ the instrument in an operation procedure. With the pivotal configuration of the coupling portion, the doctor himself can adjust the optimal ergonomic angle between the handle and the shaft, without having to exchange the handle or even the entire instrument. The handle according to the invention is therefore substantially improved with respect to ergonomics.

In providing the adjustability of the handle axis with respect to the longitudinal axis of the shaft, the problem arises that the force transmission element must be joined with the movable grip element such that the motion of the movable grip element can be translated into axial motion of the force transmission element for all angles of the handle. In the conventional handles, the force transmission element, normally formed as a push and pull rod, is directly joined with the movable grip element at its proximal end. This type of connection of the force transmission element however cannot be retained if the handle is placed at an angle with respect to the shaft. This would mean that the force transmission element in the area of the pivot axis of the coupling portion would also have to be deflected, angled or bent and a compensation for the length of the force transmission element would also be provided depending on the angle of the shaft with respect to the handle axis. The use of a flexible transmission element, for example in the form of a Bowden cable, which could adapt to the different angles in the angled region, would have the disadvantage that increased friction would arise at the deflection position. Also, when angling the shaft with respect to the handle, the movable grip element would be undesirably moved due to the constant length of the force transmission element. A Bowden cable has the further disadvantage that impurities could collect between the mantel and the flexible wire of the Bowden cable, which would be difficult or impossible to remove. Furthermore, only limited compressive forces can be translated to the movable tool with a Bowden cable.

In contrast, a force transmission mechanism is provided according to the invention between the movable grip element and the force transmission element, by which the movable grip element is or can be joined with the force transmission element by a lever arrangement. The arrangement comprises at least two double-arm levers, the first lever being pivotal about an axis stationary with respect to the handle and the second lever being pivotal about an axis stationary with respect to the coupling portion. Both levers are joined in force-locking manner with one another and pivotal about a first pivot axis with respect to one an other.

Thus instead of connecting the force transmission element directly with the movable grip element passing the first pivot axis, the handle according to the invention provides a lever arrangement comprising at least two double-arm levers between the movable grip element and the force transmission element.

Force from the movable grip element is first transmitted to the first lever, so that it is pivoted about its axis fixed to the handle and through the connection causes the second lever to pivot about it s axis fixed to the coupling portion, which in turn is joined with the force transmission element, so that it can be translated in the axial direction of the shaft. Due to the fact that the two levers are pivotal about the first pivot axis and with respect to one another, the two levers can take on an angular position relative to one an other which corresponds to the respective adjustment angle of the shaft with respect to the handle axis. Thus the same force transmission conditions are present for all angular positions, because the force transmission characteristics are only determined by the configuration of the two levers. In particular, this configuration of the force transmission mechanics has the advantage that the force transferred from the movable grip element to the force transmission element is independent of the adjustment angle between the shaft and the handle axis. A further advantage is that when actuating the movable grip element and transmitting force to the lever arrangement, the shaft can be pivoted with respect to the handle axis without having to release or inactivate the movable grip element.

In a preferred embodiment, the movable grip element is joined with a coupling rod axially displaceable in a longitudinal direction thereof, which in turn is joined with a first lever arm of the first lever.

Applying force from the movable grip element to the lever arrangement through an axially displaceable coupling rod has the advantage that applying force from the movable grip element via the coupling rod is also possible when the grip element is arranged remotely from the lever arrangement.

In a further preferred embodiment, the coupling rod is arranged such that its longitudinal axis lies on a line intersecting the first pivot axis.

This has the particular advantage that when the movable grip element is actuated, the coupling rod does not exert a torque on the coupling portion, which is pivotal about the first pivot axis. In other words, the play of the coupling portion about the first pivot axis is not transmitted to the movable grip element, so that the mechanics of force transmission from the movable grip element to the force transmission element is nearly free of play.

In a further preferred embodiment, the first lever and the second lever are joined with one another by a journal having a pivot joint, whose pivot axis is coincident with the first pivot axis.

This feature provides a constructively simple and particularly advantageous pivotal connection about the first pivot axis between the first lever and the second lever. The journal can be arranged such that its longitudinal axis is coincident with the first pivot axis. In the simplest case, the journal can consist of two journal halves joined with one another by a pivot joint, which has a rotational degree of freedom about the first pivot axis.

Preferably, the first lever converts axial motion of the coupling rod into axial motion of the journal in the direction of the first pivot axis and the second lever translates axial motion of the journal into axial motion of the force transmission element in the direction of the longitudinal axis of the shaft.

This feature allows a kinematically favorable force transmission from the coupling rod through the lever arrangement to the force transmission element. Since the lever arrangement comprises at least two levers, the lever arrangement together with the journal can be conveniently configured such that axial motion of the coupling rod is converted by the first lever into axial motion of the journal transversely to the motion direction of the coupling rod, where the axial motion of the journal can then be converted by the second lever into motion of the force transmission element transversely to the movement direction of the journal and thus in the direction of the longitudinal axis of the shaft.

In a further preferred embodiment, the coupling portion additionally is pivotal relative to the handle axis about a second pivot axis running transversely to the first pivot axis and transversely to the longitudinal axis of the shaft, and the first lever and the second lever are joined to be pivotal with respect to one another about the second pivot axis.

Of particular advantage is that the shaft is provided with two degrees of freedom with respect to the handle, i.e. the shaft can take on different angular positions with respect to the handle about the first pivot axis and in addition also about the second pivot axis. Consequently, the instrument equipped with the present handle can be even better adapted to the special requirements of the doctor operating the instrument and to the special requirements of the operative procedure. Thus, the ergonomics of the handle of the present invention is even further improved.

Preferably, a third double-arm lever is arranged between the first lever and the second lever, where the first lever is joined with the third lever to be pivotal about the first pivot axis and the second lever is pivotally joined with the third lever to be pivotal about the second pivot axis.

In constructively simple and advantageous manner, this feature provides force transmission mechanics for the configuration of the handle where the coupling portion is pivotal with respect to the handle axis about two pivot axes. A force transmission is achieved independent of the respective angle of the shaft with respect to the handle axis, also for a handle with two degrees of freedom of the coupling portion with respect to the handle axis.

In a further preferred embodiment, the first lever and/or the second lever and/or optionally the third lever are formed approximately as an L-shaped angle.

The advantage is that the force introduction into the lever and the force transmission out of the lever can take place at a right angle with respect to the corresponding lever arm, i.e. with the maximum possible torque.

In a further preferred embodiment, the first lever and the second lever and optionally the third lever are configured with respect to their lever arm ratios, such that a force enhancement results in the force transmission from the movable grip element through the lever arrangement to the force transmission element.

This feature is of particular advantage in such instruments when hard tissue is to be removed from the human or animal body, for example bone tissue. By proper selection of the lever arm ratio, such hard tissue can easily be removed with only a little hand force of the doctor.

However, it can also be preferred that the first lever and the second lever and optionally the third lever are configured with respect to their lever arm ratios, such that the lever arrangement transmits a constant or a smaller force.

This can be of advantage for example when the instrument comprises tools for grasping tissue, for example to displace organs or vessels in the body, i.e. instruments by which the doctor must carefully apply force with his hand to avoid damage to vessels or organs.

In a further preferred embodiment, the shaft is or can be joined with the coupling portion pivot about its longitudinal axis. This feature has the advantage that the shaft can not only be angled with respect to the handle, but additionally is rotatable about its longitudinal axis. The tool or tools at the distal end of the shaft can then be additionally adjusted in any rotary position with respect to the handle. The handle of the present invention in this embodiment allows a total of three degrees of freedom of motion relative to the shaft, where the instrument equipped with the handle can be even better adapted to the given requirements of the operation.

In a further preferred embodiment, the force transmission element is directly or indirectly joined with the second lever through a ball and socket connection.

This feature is of particular advantage with the above embodiment where the shaft is or can be pivotally joined with the coupling portion about its longitudinal axis, since the force transmission element also rotates when rotating the shaft about its longitudinal axis because the ball and socket connection with the second lever allows such rotation. The force transmission element is joined with the at least one movable tool at the distal end of the shaft and on the other hand, at least one movable tool in operational condition of the instrument is fixedly joined with the shaft. Consequently, a rotational capability of the shaft about its longitudinal axis is achieved in constructively simple manner because no additional elements are required to connect the force transmission element pivotally with the at least one movable jaw.

In a further preferred embodiment, the coupling portion can be locked by means of a locking mechanism in a plurality of angular positions with respect to the handle axis in an angular range of up to 240° about the first pivot axis and/or about the second pivot axis.

With this feature, the handle can be pivoted in an angular range between about −120° and about +120° about the first pivot axis and/or about the second pivot axis and can be locked in at least two, preferably however a plurality of pivot positions, whereby the ergonomics of the handle with respect to the shaft angle can be adapted over a large angular range to the desired requirements of the doctor. The pivotal range however can also be smaller, for example between −90° and +90° or between 0° and +120° just to mention a few examples.

Preferably, the locking mechanism comprises a locking nose engageable with notches in the coupling portion and the locking mechanism further comprises a push button such that the locking nose is disengageable with the respective notch by depressing the push button.

This type of locking or unlocking the coupling portion leads in advantageous manner to pivoting and locking characteristics of the handle which are easy to manipulate.

In a further preferred embodiment, the coupling portion comprises a seat for the shaft for releasably joining the shaft with the coupling portion.

The advantage is that the shaft can be removed from the coupling portion and therefore from the handle, where the handle and the shaft can be better cleaned when separated.

In a further preferred embodiment, the coupling portion comprises a seat for a proximal end of the force transmission element, where the seat is axially movable and joined with the second lever.

In this embodiment, the force transmission element is not directly joined with the second lever, but through a separate receptor provided for the proximal end of the transmission element. The advantage is that the connection between the force transmission element and the second lever can be made very easily. In addition, the embodiment allows the possibility of connecting the force transmission element releasably with the handle.

Preferably, the seat comprises a locking mechanism for releasably joining the force transmission element with the coupling portion. The advantage is that the force transmission element can be removed from the coupling portion and thus from the handle, where the force transmission element after removal from the handle can be easily cleaned.

An instrument according to the present invention, which comprises a shaft, at least one movable tool at the distal end of the shaft and a force transmission element arranged to be axially movable with respect to the shaft for actuating the at least one movable tool, is preferably and advantageously equipped with a handle of the invention according to one or more of the above embodiments.

Preferably, the shaft and/or the force transmission element is releasably joined with the handle and/or the force transmission element is releasably joined with the shaft. Due to the releasable configuration of both the shaft and the force transmission element, the shaft, the force transmission element and the handle can be disassembled from the instrument, where each component can then be efficiently cleaned.

Further features and advantages will be apparent from the following description and the attached drawings.

It will be understood that the above-mentioned features and those to be discussed below are not only applicable in the given combinations, but may also be employed in other combinations or taken alone without departing from the scope of the invention.

Embodiments of the invention are illustrated in the drawings and will be discussed in more detail below.

BRIEF DESCRIPTION OF THE DRAWINGS

FIG. 5a is a side view, FIG. 5b) a plan view in a first operational position of the transmission mechanism and FIG. 5c) a plan view of the transmission mechanism in a second operational position;

FIG. 7 shows a side view of a push button of the locking mechanism for locking the coupling portion.

DETAILED DESCRIPTION OF PREFERRED EMBODIMENTS

Figure 1:
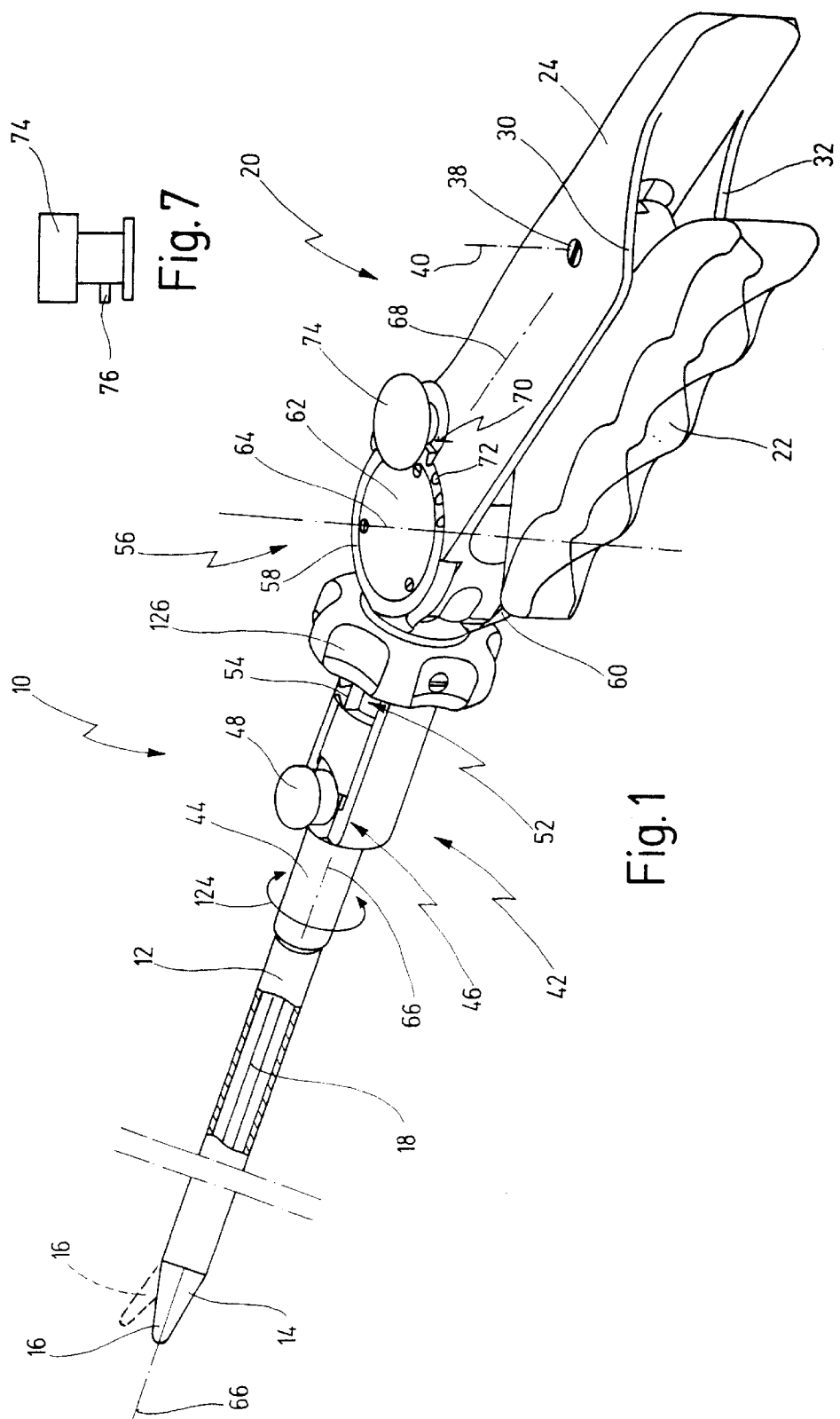
FIG. 1 shows a perspective total of view of an instrument equipped with a handle according to the present invention.

A medical instrument is shown in FIG. 1 generally designated with numeral 10, which is used for surgical operations on the human or animal body, for example for preparing or treating tissue.

The instrument 10 comprises an elongated shaft 12 in the form of a tubular shaft, so that the instrument 10 can be considered to be a tubular shaft instrument. A first tool 14 and a second tool 16 are arranged at the distal end of the shaft 12. The second tool 16 is movable relative to the first tool 14 and pivoted on the shaft 12 for this purpose.

The first tool 14 and the second tool 16 are formed as jaw parts, which have a cutting function for separating tissue.

A force transmission element 18 extends within the shaft 12, which is joined in force-locking manner with the second movable tool 16 to cause the tool to open and close. The open position of the movable jaw part 16 is illustrated with dashed lines in FIG. 1. The force transmission element 18 is axially movable with respect to the shaft 12 and is arranged therein.

The instrument 10 comprises a handle 20 at the proximal end of the shaft 12 which will be described in the following with reference to FIGS. 1 to 4. Furthermore, FIGS. 5a) to 5c) show schematic diagrams of the operating principle of the force transmission mechanism from the handle 20 to the force transmission element 18.

Figure 2:
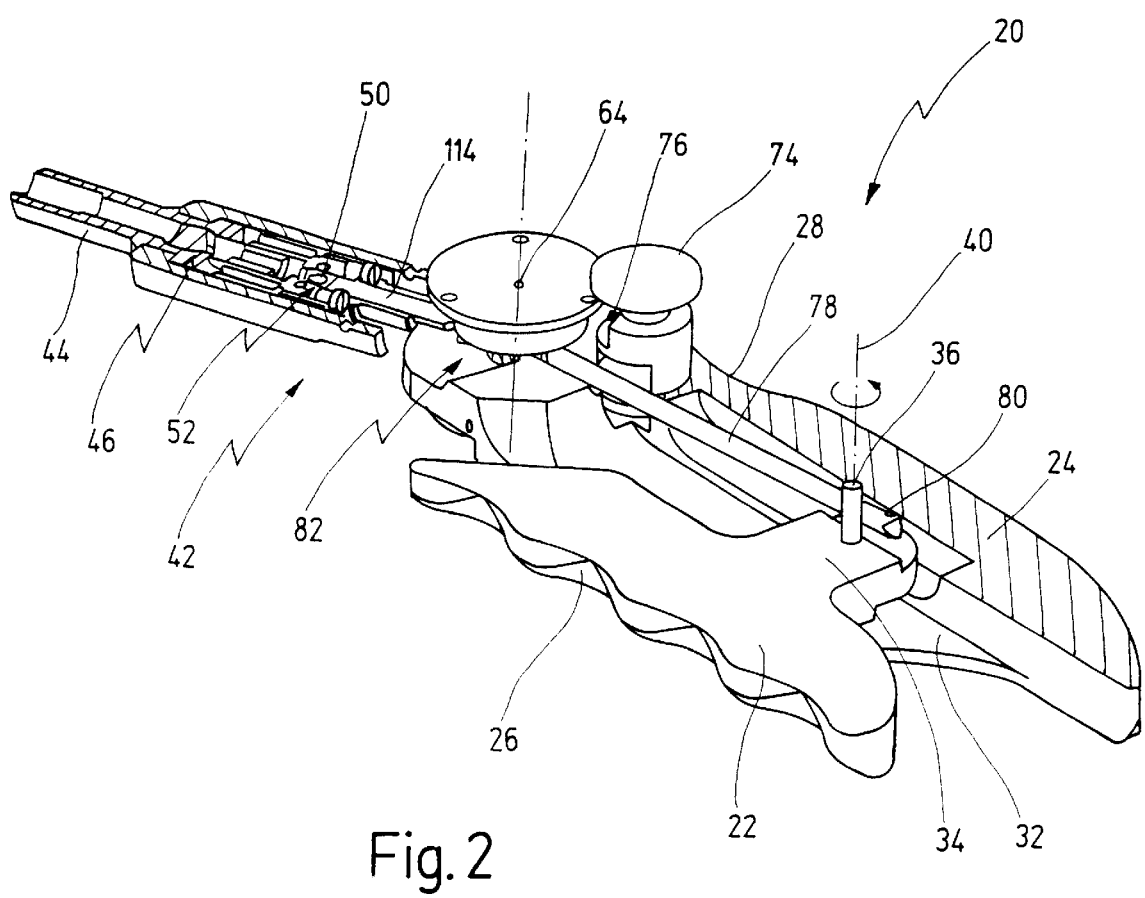
FIG. 2 shows the handle of FIG. 1 in a partial cross section and perspective view, where parts are left out compared to FIG. 1.

According to FIGS. 1 and 2, the handle 20 comprises a movable grip element 22 and an immovable grip element 24. The movable grip element 22 comprises four finger wells 26 for the index, middle, ring and the little finger. The immovable grip element portion 24 correspondingly comprises a thumb well 28 for the thumb.

The bushing 36 and the screw 38 define a pivot axis 40, about which the movable grip element 22 is pivotal with respect to the immovable grip element 24.

The handle 20 further comprises a coupling portion 42 at its distal end with which the shaft is or can be joined with the handle 20. For this purpose, a proximal end of the shaft 12 is inserted into the distal end of a tube 44 of the coupling portion 42 and locked by means of a locking mechanism 46 with the coupling portion 42, which has a push button 48 for releasing the locked condition. The locked condition between the shaft 12 in the coupling portion 42 can be released by depressing the button 48 to be able to remove the shaft 12 from the coupling portion 42.

The force transmission element 18, which is joined in force-locking manner at its distal end to the movable tool 16, is also inserted with its proximal end (not shown) in the tube 44 of the coupling portion 42 and is releasably received in a seat 50 in the tube 44. For this purpose, the force transmission element 18 at its proximal end comprises a ball-like expanded portion, which is passed in form-fit manner into the seat 50. For reliable connection of the proximal end of the force transmission element 18 to the seat 50, a locking mechanism 52 is provided on the coupling portion 42, which includes a button 54. By depressing the button 54, the force transmission element 18 can be withdrawn from the seat 50 in the distal direction.

The seat 50 is axially shiftable relative to the tube 44 and is biased toward its proximal end position by means of a spring (not shown).

The coupling portion 42 at its proximal end comprises a bifurcated end portion 56, through which the coupling portion 42 is secured to the immovable grip element 24. The end portion 56 comprises a first branch portion 58 as well as an opposite second branch portion 60, both of which are provided in the form of a circular ring.

The end portion 56 of the coupling portion 42 is securely joined with the immovable grip element 24 of the handle 20 by means of a round plate 62, which is fitted into the branch portion 58. The branch portion 60 is also joined with the immovable grip element 24 by means of a corresponding round plate, not shown in FIG. 1.

The proximal end portion 56 of the coupling portion 42 is pivotal relative to the grip elements 22, 24 about a first pivot axis 60, which passes centrally through the proximal end portion 56, wherein the first pivot axis 64 is transverse to a longitudinal axis 66 of the shaft 12. In the present embodiment, the first pivot axis 64 is perpendicular to the longitudinal axis 66 of the shaft 12. With the pivoting of the coupling portion 42 about the first pivot axis 64, the coupling portion 42 and the shaft 12 coupled thereto can be disposed at an angle relative to a handle axis 68 in a plurality of different angular positions. The shaft 12, or precisely its longitudinal axis 66, can thus take on various angular positions selectively with respect to the handle axis 68, namely angles between about 0° and about 60°, so that in the present embodiment, the maximum angular displacement between the handle axis 68 and the longitudinal axis 66 of the shaft 12 is about 60°. However, it may be appropriate for other instruments using the handle 20 to configure the coupling portion 42 to be pivotal in a total angular range of about 240°, for example between −120° and +120°.

The coupling portion 42 is lockable in the selected angular position with respect to the handle axis 68, namely by means of a locking mechanism 70. The locking mechanism 70 includes a plurality of notches 72, distributed about the periphery of the branch portion 58 of the end portion 56 of the coupling portion 42. The locking mechanism 70 further includes a push button 74 arranged on the stationary grip element 24 and a locking nose 76 as seen in FIG. 7, which is engageable with one of the respective notches 72. The push button 74 is urged by a spring toward a position in which the locking nose 76 engages one of the notches 72. By depressing the push button 74, the locking nose 56 is disengaged from the notch 72 in which it is currently disposed, so that when the button is depressed, the coupling portion 42 can be rotated about the first pivot axis 64 relative to the handle axis 68.

The mechanics of force transmission of the handle 20 will be described in the following, where a hand force exerted by the operator on the movable grip element 22 is transferred from the movable grip element 22 to the force transmission element 18 through a pivotal connection of the coupling portion 42 with the immovable grip element 24 and the movable grip element 22 in any angular position of the coupling portion 42 and thus any position of the longitudinal axis 66 of the shaft 12 relative to the handle axis 68.

Figure 3:
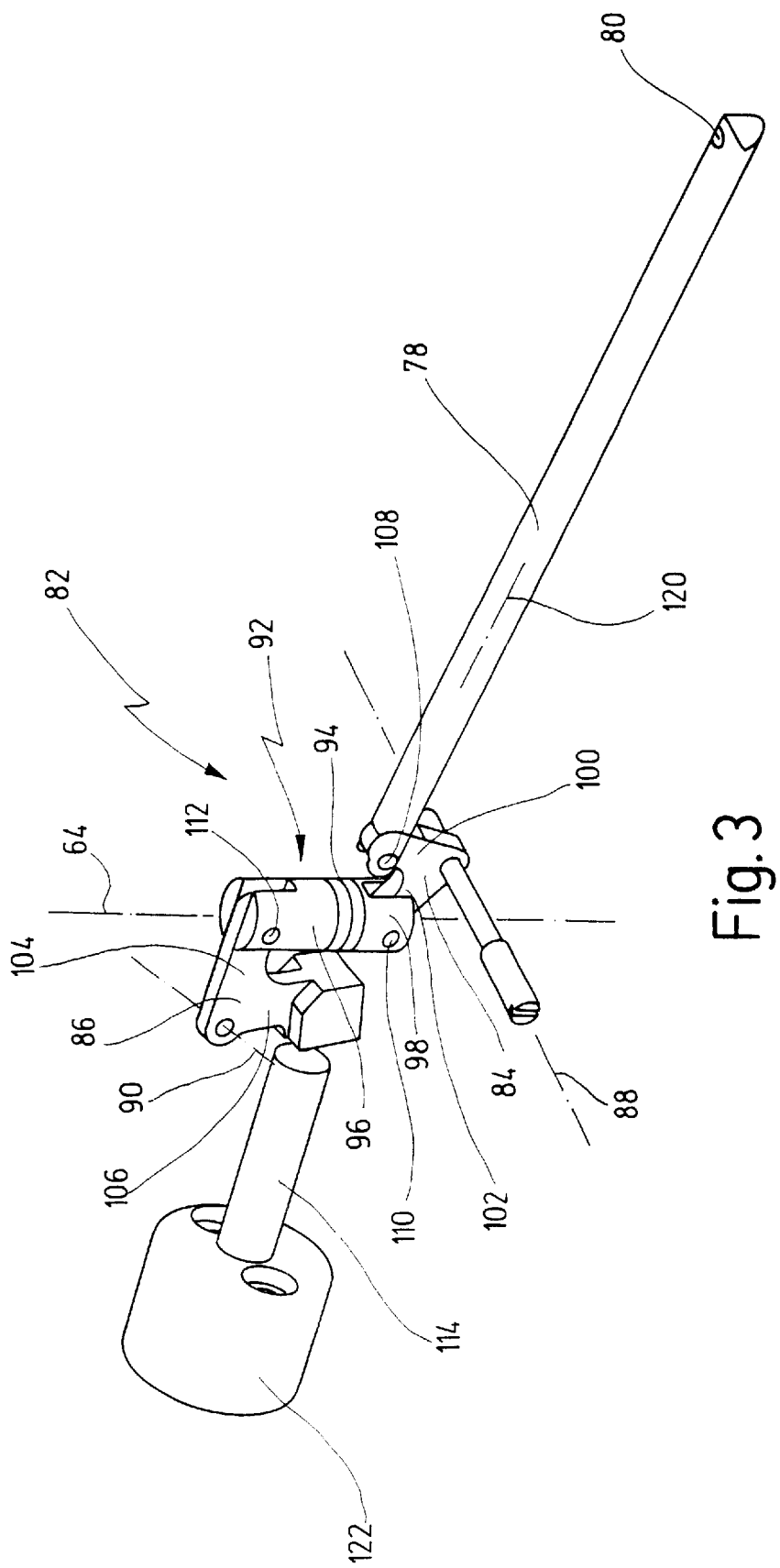
FIG. 3 shows a perspective view of a force transmission mechanism of the handle for transmitting force from the movable grip element to a force transmission element of the instrument in FIG. 1.
Figure 4:
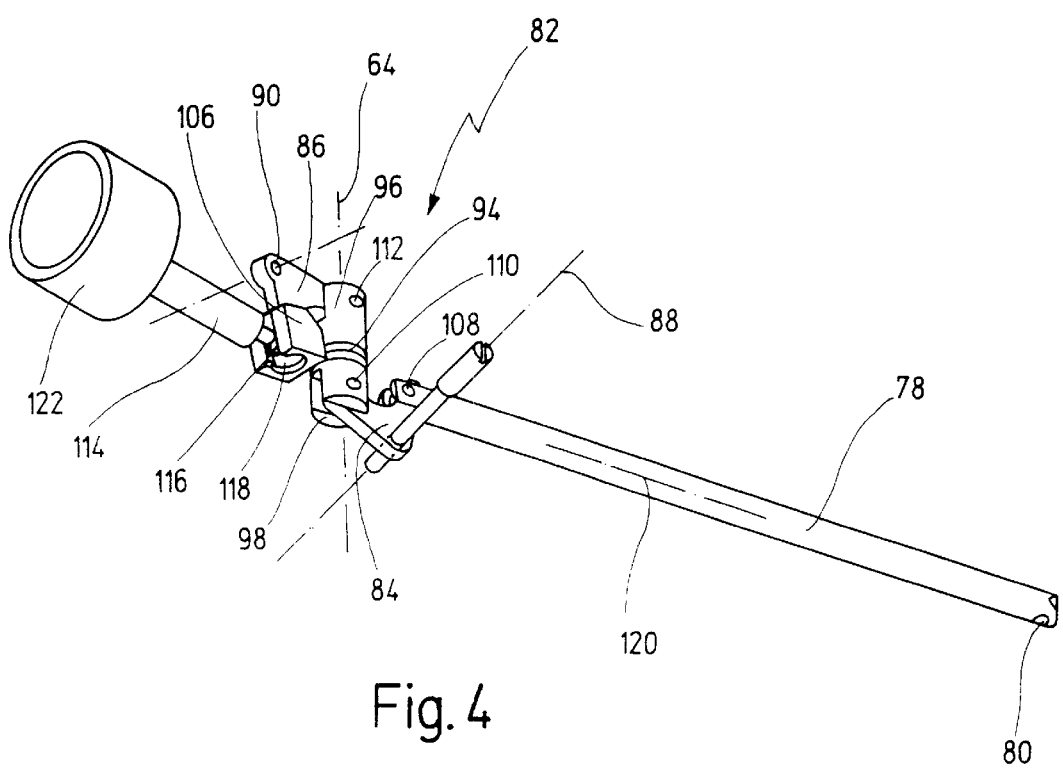
FIG. 4 shows a different perspective of the force transmission mechanism of FIG. 3.
Figure 5:
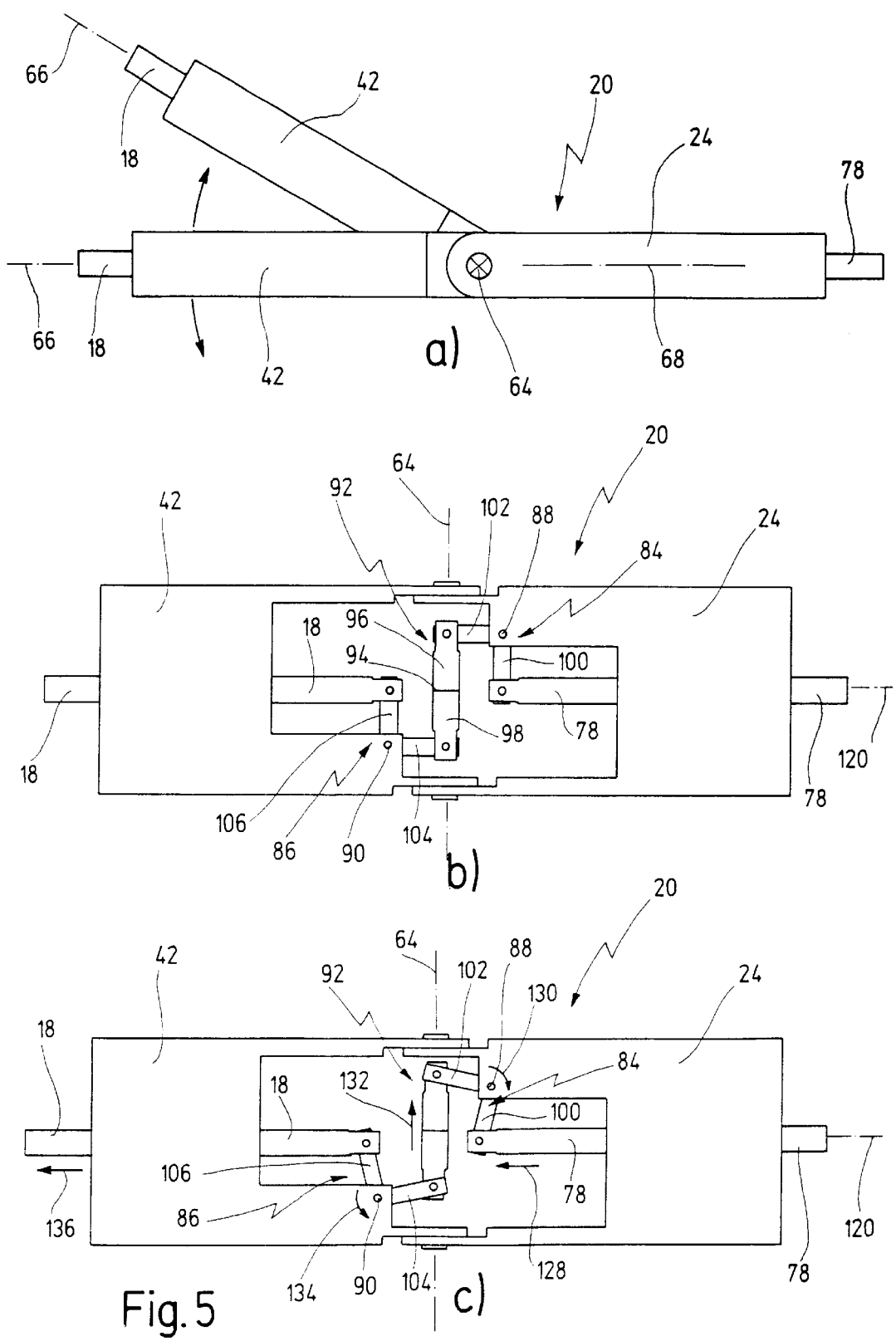
FIGS. 5a) to 5c) show a schematic representation of the principle of the force transmission mechanism of the handle in FIG. 2, where

The force transmission mechanism can be taken from FIGS. 2 to 4.

A coupling rod 78 is coupled with its proximal end at a linking point 80 onto the linking portion 34 of the movable grip element 22 outside of the pivot axis 40. A rotation of the movable grip element about the pivot axis 40 then causes linear motion of the coupling rod 78 in its longitudinal direction toward the distal end.

The movable grip element 22 is connected through the coupling rod 78 to a lever arrangement 82. The lever arrangement 82 comprises a first lever 84 and a second lever 86.

The first lever 84 is fixed on the immovable grip element 24 between the branch portions 58, 60 of the end portion 56 of the coupling portion 42 to be pivotal about a first axis 88 stationary with respect to the handle.

The second lever 86 is secured to the branch portions 58, 60 of the end portion 56 of the coupling portion 42 to be pivotal about a second axis 90 stationary with respect to the coupling portion 42, i.e. the second lever 86 is rotated along with a rotation of the coupling portion 42 about the first pivot axis 64, so that for any given angular position of the coupling portion 42 with respect to the handle axis 68, the axis 88 fixed to the handle and the axis 90 fixed to the coupling portion form a corresponding angle with respect to one another.

The first lever 84 and the second lever 86 are pivotally joined with one another about the first pivot axis 64. The pivotal connection of the first lever 84 with the second lever 86 is accomplished with a journal 92, which comprises a pivot joint 94. The journal 92 is formed of a first journal part 96 and a second journal part 98, which can be pivoted counter-directionally with respect to one another about the first pivot axis by means of the pivot joint 94.

The journal 92 itself is arranged such that the first pivot axis 64 passes approximately centrally through the journal 92.

The first lever 84 and the second lever 86 are each formed as double-arm levers, where the first lever 84 comprises a first lever arm 100 as well as a second lever arm 102 and the second lever 86 comprises a first lever arm 104 as well as a second lever arm 106.

The first lever 84 and the second lever 86 are each formed as L-shaped angles, i.e. the lever arms 100 and 102 or 104 and 106 are disposed approximately at right angles.

The first lever arm 100 and the second lever arm 102 of the first lever 84 are approximately of equal length, as are the first lever arm 104 and the second lever arm 106 of the second lever 86.

The coupling rod 78 is coupled at a linking point 108 to the first lever arm 100 of the first lever. The second lever arm 102 of the first lever is coupled at a linking point 110 to the journal part 98 of the journal 92. The first lever arm 104 of the second lever 86 is coupled at a linking point 112 to the journal part 96 of the journal 92.

A further coupling rod 114 is joined with the second lever arm 106 of the second lever 86, namely by means of a ball and socket connection, wherein the proximal end of the further coupling rod 114 comprises a ball 116, which is reliably and loose-proof received in the ball socket 118 of the second lever arm 106 of the second lever 86. The coupling rod 114 is joined with the seat 50 as shown in FIG. 2, in which the proximal end of the force transmission element 18 is received. The coupling rod 114 therefore is always disposed in straight line extension with the force transmission element 18, however forms a different angle with the longitudinal axis 120 of the coupling rod 78 depending on the adjusted angle between the coupling portion 42 and the handle axis 68. The lever arrangement 82 then allows force transmission through the angle.

The further coupling rod 114 is passed through a fixed bushing 122 in the tube 44 of the coupling portion 42 and is connected there with the seat 50 for the force transmission element 18.

The coupling rod 78 is arranged on the handle 20 such that its longitudinal axis 120 always lies on a straight line which intersects the first pivot axis 64, so that the coupling rod 78 does not exert a torque on the lever arrangement 82 with respect to the first pivot axis 64. Similarly, the further coupling rod 114 is arranged so that it is directed toward the pivot axis 64.

Returning to FIG. 1, the tube 44 of the coupling portion 42 is also rotatable about the longitudinal axis 66 as shown by the double arrow 124, and thus about the longitudinal axis of the tube 44 relative to the end portion 56 of the coupling portion 42. The tube 44 and therefore the shaft 12 can be rotated by an amount of 360° in both rotary directions about the longitudinal axis 66 of the shaft 12. An adjustment wheel 126 is also arranged on the tube 44 to rotate the tube 44, which can be operated with the thumb for rotating the shaft 12. When rotating the tube 44 and therefore the shaft 12 about the longitudinal axis 66 of the shaft 12, the force transmission element 18 is also rotated, which is made possible by the ball and socket connection of the further coupling rod 114 to the second lever arm 106 of the second lever 86.

With reference to FIGS. 5a) to 5c), the function of the mechanics of force transmission of the handle 20 is described in more detail. FIGS. 5a) to 5c) show the handle 20 in highly schematic representation, where the immovable grip element 24 and the coupling portion 42 are shown as blocks for simplification. First of all, FIG. 5a) shows the pivoting of the coupling portion 42 relative to the handle axis 68 about the first pivot axis 64. When pivoting the coupling portion 42 about the first pivot axis 64, the first journal part 96 is also rotated about the first pivot axis 64 relative to the second journal part 98 of the journal 92, without the journal part 96 being separated from the journal part 98. This means that a force-locking connection exists between the coupling rod 78 and the force transmission element 18 during the pivoting of the coupling portion 42. For this reason, the shaft 12 can be displaced to another angular position with respect to the handle axis 68 even during an operation when the movable tool 16 is moved by actuation of the movable grip element 22.

FIG. 5b) shows the rest condition of the force transmission mechanism, i.e. when the tools 14, 16 in FIG. 1 are closed. Starting from this rest position, when the movable grip element 22 is actuated the coupling rod 78 is displaced in distal direction along its longitudinal axis in the direction of the arrow 128. The coupling rod 78 engages the first lever arm 100 of the first lever 84 and pivots the first lever 84 about the axis 88 fixed to the handle in the direction of the arrow 130. By pivoting the first lever 84, the second lever arm 102 of the first lever 84 moves the journal 92 in the direction of the arrow 132, i.e. in the direction of its longitudinal axis or in the direction of the first pivot axis 64. The second lever 86 is pivoted about the axis 90 fixed to the coupling portion in the direction of the arrow 134 because the journal 92 also engages with the first lever arm 104 of the second lever 86.

The second lever arm 106 of the second lever 86, which is joined with the force transmission element 18, moves the force transmission element 18 in the direction of the arrow 136 also toward the distal end, whereby the movable tool 16 at the distal end of the shaft 12 is moved. When replacing the movable grip element 22, the biasing of the receptor 50 for the force transmission element 18 causes the force transmission mechanism to return to its rest position illustrated in FIG. 5b).

A further embodiment of a handle 20' is shown in FIGS. 6a) to 6c) in a highly schematic illustration comparable to that of FIGS. 5a) to 5c). Similar parts are designated with the same reference numeral but with signs.

The handle 20' again comprises a coupling portion 42' pivotable relative to a handle axis 68' about a first pivot axis 64'.

The coupling portion 42' is additionally pivotal relative to the handle axis 68' about a second pivot axis 138, where the second pivot axis 138 runs transversely to the first pivot axis 64' and transversely to a longitudinal axis 66' of the shaft (the shaft is not shown). The coupling portion 42' thus is pivotal with respect to the handle axis 68' in the direction of the arrows 140, 142 about the second pivot axis 138 and in the direction of the arrows 144, 146 about the first pivot axis 64'.

Compared to the coupling portion 42, the coupling portion 42' is modified by an intermediate piece 148, which connects the coupling portion 42' pivotally with the immovable grip element 24' on the one hand about the first pivot axis 64' and on the other hand about the second pivot axis 138.

The force transmission mechanism from the coupling rod 78', corresponding to the coupling rod 78 in the previous embodiment, to the force transmission element 18', corresponding to the force transmission element 18 of the previous embodiment, is also slightly modified as will be discussed below.

The force transmission element 18' and the coupling rod 78' are again joined with one another by a lever arrangement 82', which comprises a first lever 84' joined with the coupling rod 78' and a second lever 86' joined with the force transmission element 18'. The first lever 84' and the second lever 86' are again double-arm levers provided in the form of an L-shaped angle.

The first lever 84' and the second lever 86' are again joined with be pivotal about the first pivot axis 64'. The first lever 84' is pivotally mounted about an axis 88' fixed to the handle and the second lever 86' is pivotally mounted about an axis 90' fixed to the coupling portion.

The first lever 84' and the second lever 86' are also mounted to be pivotal about the second pivot axis 138, in addition to the first pivot axis 64'.

The connection between the first lever 84' and the second lever 86' is accomplished by a third lever 150 also having two arms, which is mounted on the intermediate piece 148 to pivot about an axis 152 fixed to the intermediate piece.

The third lever 150 comprises two lever arms 154, 156 disposed at a right angle to one another, where the lever arm 154 comprises a ball 158 at its free end and the lever arm 156 comprises a ball 160 its free end.

The ball 158 of the lever arm 154 engages in a slotted end of the second lever arm 102' of the first lever 84' and is pivotal therein relative to the first lever 84' about the first pivot axis 84'.

The ball 160 of the second lever arm 156 engages in a slotted end of the first lever arm 104' of the second lever 86' and is pivotal therein relative to the second lever 86' about the second pivot axis 138. The connection of the third lever 150 with the first lever 84' and the second lever 86' guarantees that the coupling portion 42' can be pivoted without separating the connection of the coupling rod 78' with the force transmission element 18' about the first pivot axis 84' and about the second pivot axis 138.

In this embodiment, the coupling rod 78' is also arranged such that it lies on a line which intersects both the first pivot axis 84' and the second pivot axis 138, so that the coupling rod 78' does not exert a torque on the coupling portion 42' either with respect to the first pivot axis 64' or with respect to the second pivot axis 138.

If the coupling rod 78' is moved axially in the direction of the arrow 162, the first lever 84' rotates about the axis 88' fixed to the handle in the direction of the arrow 164. The second lever arm 102' of the first lever 84', which engages the first lever arm 154 of the third lever 150, pivots the third lever about the axis 152 fixed to the intermediate piece in the direction of an arrow 166 (see FIGS. 6a) and 6c)).

The second lever arm 156 of the third lever 150, which engages with the second lever 86', pivots the lever 86' about the axis 90' fixed to the coupling portion in the direction of the arrow 168, whereby the force transmission element 18' is axially urged in the distal direction of the arrow 170.

Figure 6:
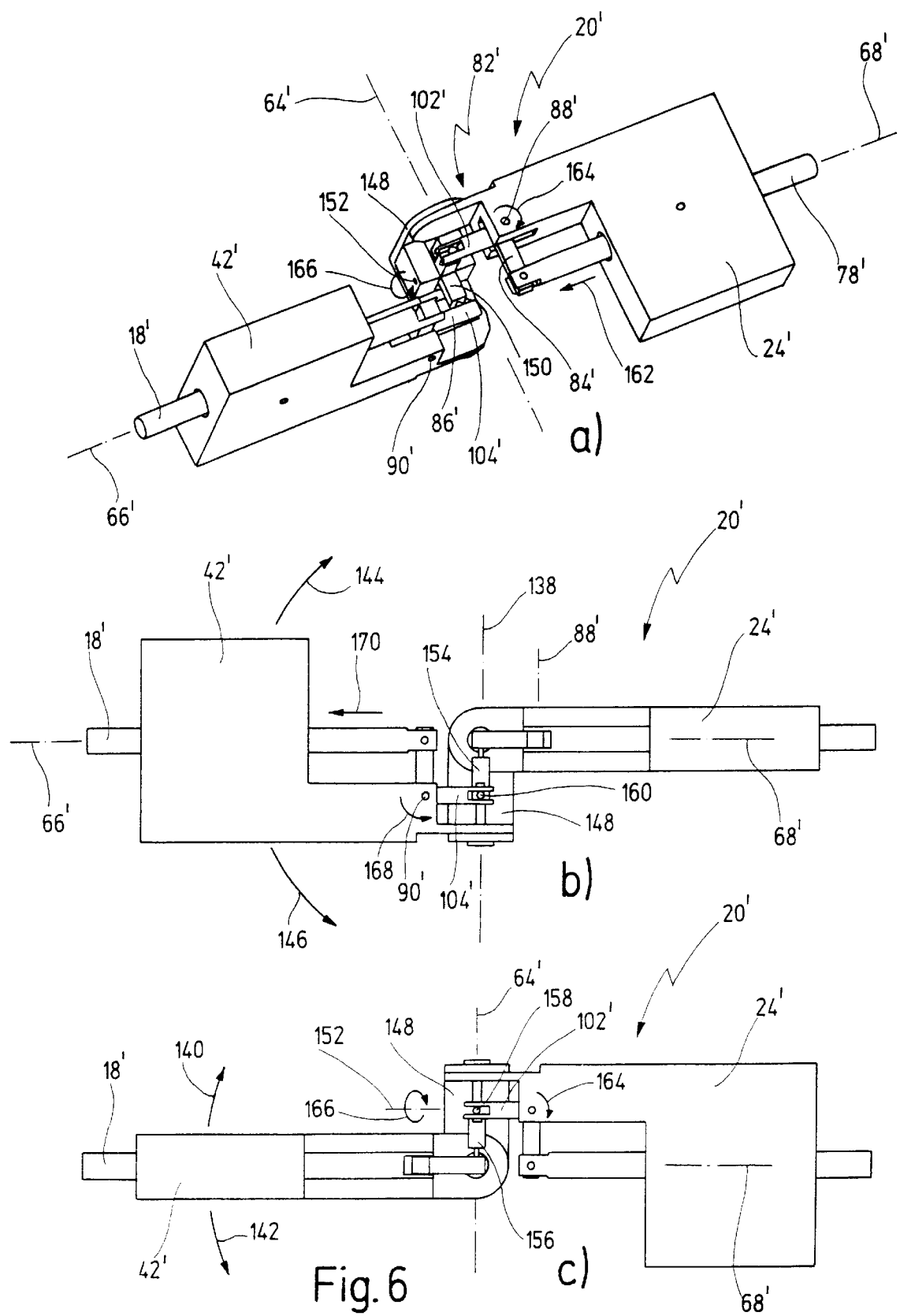
FIGS. 6a) to 6c) show a schematic illustration of the principle of a force transmission mechanism for a handle, whose coupling portion is pivotal about two pivot axes with respect to the handle axis, where FIG. 6a) is perspective view, FIG. 6b) a side view and FIG. 6c) a plan view of the transmission mechanism.

In the lever arrangement 82 of the embodiment of FIGS. 1 to 5 as well as the lever arrangement 86' of the embodiment of FIG. 6, the levers of the respective arrangements have lever arm ratios such that a constant force is translated by the arrangements 82', 82 from the coupling rods 78', 78 to the force transmission elements 18, 18'.

However, it is also contemplated that the individual levers of the arrangements 82 and 82' be formed with lever arm ratios, such that the force transmission from the coupling rods 78, 78' through the lever arrangements 82, 82' to the force transmission elements 18, 18' results in a force enhancement.

Returning to FIG. 1, the instrument 10 can be disassembled into the handle 20, the shaft 12 and the force transmission element 18. The releasable connection between the shaft 12 and the handle 20 as well as between the force transmission element 18 and the handle 20 has been described above. However, the force transmission element 18 can be removed from the shaft 12 by providing a releasable connection of these parts by means of a bayonet-like connection in the region of the tools 14, 16.

Although the force transmission element 18 in the above examples operates with compressive forces, the force transmission mechanism of the present invention can easily be adapted with slight modifications such that the force transmission element 18 works with tensile forces. In addition, the force transmission from the movable grip element 22 to the lever arrangement 82, which requires a pushing of the coupling rod 78, can be replaced by a pulling of the coupling rod 78 by a corresponding modification.

In addition, the invention can also be used with scissor-like grip elements in an advantageous manner.

What is claimed is:

1. A handle for a medical instrument, comprising:
   at least one movable grip element for being joined with a force transmission element axially movable in direction of a longitudinal axis of a shaft of said instrument to transfer motion of said at least one movable grip element into linear motion of said force transmission element;
   a coupling portion for joining said shaft with said handle, said coupling portion being pivotal relative to a handle axis about at least one first pivot axis running transversely to the longitudinal axis of said shaft;
   a lever arrangement for joining said at least one movable grip element with said force transmission element, comprising at least two double-arm levers, a first lever of which being pivotal about a first axis stationary with respect to said handle and a second lever of which being pivotal about a second axis stationary with respect to said coupling portion, and said two levers being joined to another to be pivotal with respect to one another about said first pivot axis.

2. The handle of claim 1, wherein said movable grip element is joined with a coupling rod axially displaceable along a longitudinal direction thereof, which in turn is joined with a first lever arm of said first lever.

3. The handle of claim 2, wherein said coupling rod is arranged such that said longitudinal axis thereof lies along a line intersecting said first pivot axis.

4. The handle of claim 1, wherein the first lever and said second lever are joined with one another by a journal having a pivot joint whose pivot axis is coincident with said first pivot axis.

5. The handle of claim 4, wherein said movable grip element is joined with a coupling rod axially displaceable along a longitudinal direction thereof, which in turn is joined with a first lever arm of said first lever and wherein the first lever translates axial motion of said coupling rod into axial motion of said journal in the direction of said first pivot axis and wherein said second lever translates said axial motion of said journal into axial motion of the force transmission element in the direction of said longitudinal axis of said shaft.

6. The handle of claim 1, wherein said coupling portion additionally is pivotal relative to said handle axis about a second pivot axis, which runs transversely to said first pivot axis and transversely to said longitudinal axis of said shaft and wherein said first lever and said second lever are also joined to be pivotal with respect to one another about said second pivot axis.

7. The handle of claim 6, wherein a third double-arm lever is arranged between said first lever and said second lever, where said first lever is joined with said third lever to be pivotal about said first pivot axis and said second lever is joined with said third lever to be pivotal about said second pivot axis.

8. The handle of claim 1, wherein said first lever and/or said second lever are formed approximately as an L-shaped angle.

9. The handle of claim 1, wherein a third double-arm lever is arranged between said first lever and said second lever, where said first lever is joined with said third lever to be pivotal about said first pivot axis and said second lever is joined with said third lever to be pivotal about said second pivot axis and wherein said third lever is formed approximately as an L-shaped angle.

10. The handle of claim 1, wherein said first lever and said second lever are configured with respect to their lever arm ratios, such that a force enhancement results in the force transmission from said movable grip element through said lever arrangement to said force transmission element.

11. The handle of claim 1, wherein said first lever and said second lever are configured with respect to their lever arm ratios, such that a constant or smaller force is translated through said lever arrangement.

12. The handle of claim 1, wherein said shaft is or can be joined with said coupling portion to pivot about said longitudinal axis of said shaft.

13. The handle of claim 1, wherein said force transmission element is directly or indirectly joined with said second lever through a ball and socket connection.

14. The handle of claim 1, wherein said coupling portion can be locked by means of a locking mechanism in a plurality of angular positions with respect to said handle axis in an angular range of up to about 240° about said first pivot axis and/or about said second pivot axis.

15. The handle claim 14, wherein said locking mechanism comprises a locking nose engageable with notches in said coupling portion, and wherein said locking mechanism further comprises a push button, such that said locking nose is disengageable from said respective notch by depressing said button.

16. The handle of claim 1, wherein said coupling portion comprises a seat for said shaft for releasably joining said shaft with said coupling portion.

17. The handle of claim 1, wherein said coupling portion comprises a seat for a proximal end of said force transmission element, wherein said seat is axially movable and joined with said second lever.

18. The handle of claim 17, wherein said seat comprises a locking mechanism for releasably joining said force transmission element with said coupling portion.

* * * * *